United States Patent [19]

Waguespack et al.

[11] Patent Number: 4,922,053
[45] Date of Patent: May 1, 1990

[54] PROCESS FOR ETHYLBENZENE PRODUCTION

[75] Inventors: James N. Waguespack; James R. Butler, both of Houston, Tex.

[73] Assignee: Fina Technology, Inc., Dallas, Tex.

[21] Appl. No.: 357,381

[22] Filed: May 24, 1989

[51] Int. Cl.$^5$ .................... C07C 2/64; C07C 2/68
[52] U.S. Cl. ........................ 585/449; 585/467
[58] Field of Search .................... 585/449, 467

[56] References Cited

U.S. PATENT DOCUMENTS 2,904,607  9/1959  Mattox et al. .................... 585/467
4,107,224  8/1978  Dwyer .............................. 585/467

Primary Examiner—Helen M. S. Sneed
Assistant Examiner—James A. Saba
Attorney, Agent, or Firm—Michael J. Caddell; John K. Abokhair; M. Norwood Cheairs

[57] ABSTRACT

A process is disclosed for producing ethylbenzene from the catalytic alkylation of benzene in a multibed reactor wherein a portion of the normal overhead polyethylbenzene recycle stream is diverted into a lower section of the reactor to increase conversion and lower xylene by-product production.

11 Claims, 1 Drawing Sheet

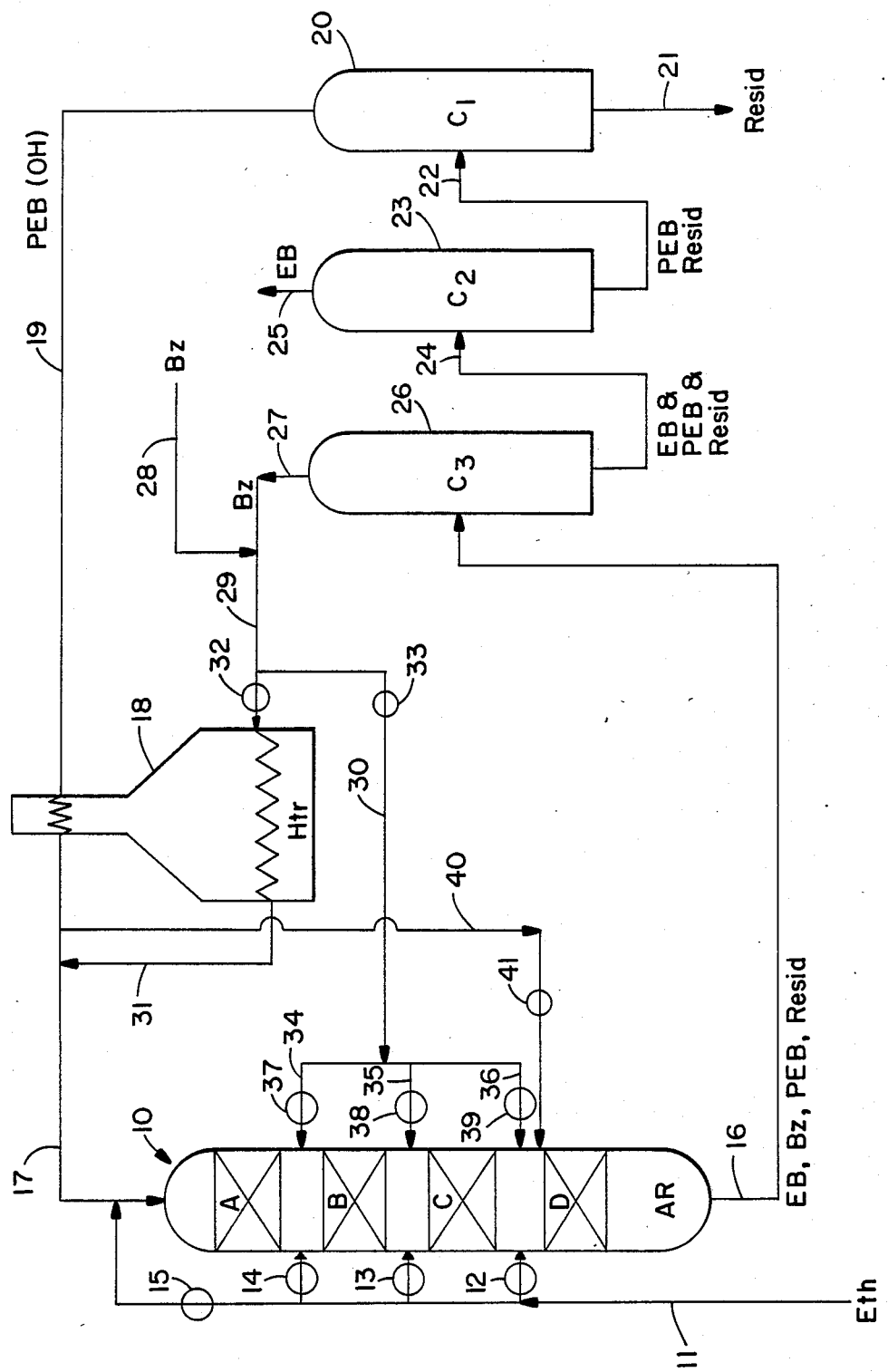

4,922,053

PROCESS FOR ETHYLBENZENE PRODUCTION

FIELD OF THE INVENTION

This invention relates to a process for producing ethylbenzene by contacting suitable reactant under specified conversion conditions in the presence of appropriate catalysts. In another aspect, this invention relates to ethylbenzene production in which unwanted by-products, especially xylene, are suppressed while acceptable conversion and selectivity to desired ethylbenzene product are maintained by diverting at least part of the Polyethylbenzene overhead recycle stream into the alkylation reactor to serve as a quench.

BACKGROUND INFORMATION

Ethylbenzene (EB) is used predominantly for the production of styrene monomer obtained through dehydrogenation. Presently much of the EB being produced is obtained by alkylation of benzene (Bz) with ethylene (Eth) under a variety of alkylation conditions. One type of alkylation process which is conventional is to employ relatively high pressures and temperatures to obtain vapor phase reaction conditions wherein the ethylene and benzene are converted in the presence of catalytic materials. Both single and multiple catalyst bed processes are well known in the art.

For example, U.S. Pat. No. 4,400,570 to Butler et al, discloses a process for manufacturing ethylbenzene for use in styrene wherein ethylene and benzene are reacted with stream over a TEA-silicate catalyst. One problem in the production of EB by such methods is the production of unwanted by-products which can be very detrimental because some of the by-products may be very difficult, or impossible, to separate from the desired EB product. Thus, as an example, the production of xylene in these types of processes is very undesirable since separation of xylene from the EB product is very difficult from a processing standpoint. In addition to the requirement that the catalyst employed in such processes be selective to the desired EB product it is also desirable to obtain acceptable conversion of the reactants to alkylated products. The ability of different catalyst materials to convert the raw feed materials into products is sometimes referred to as its "activity". "Conversion" is normally measured as a percentage of the amount of feed materials which will be converted into products during the reaction. The ability of the catalyst to maintain high conversion rates (i.e. retain activity) is very important.

Deactivation of catalysts is one major problem in catalytic alkylation processes since, even if high conversion rates are obtained initially, the failure to maintain good conversion over a long period of time requires expensive catalyst changeouts and/or regeneration procedures.

Another critical area in the formation and production of EB is in the feed/product ratio. Any factors which can significantly lower the feed/product ratios without degrading activity or conversion, and without increasing xylene production, is very desirable.

Thus it would be desirable to obtain a process in which conversion of reactants to EB can be obtained without production of unwanted xylene by-products and without the necessity of frequently regenerating or replacing the catalytic material employed.

SUMMARY OF THE INVENTION

It has now been discovered that alkylation of benzene with ethylene under vapor phase reaction conditions can be effected in a process having high conversion rates and low rates of deactivation with excellent selectivity to EB and a reduced amount of xylene formation by diverting a portion of the Polyethyl Benzene Overhead (PEB/OH) recycle stream as a quench in the alkylation reactor. More specifically, it has been discovered that by introducing part of the PEB/OH recycle stream into a reaction zone of a multizone reactor, excellent conversion to EB is achieved and a substantial reduction in the amount of xylenes is obtained.

Thus, in general, the present invention provides a method for producing ethylbenzene by reacting benzene and an ethylating agent in the presence of appropriate catalysts in a multizone reactor and utilizing a portion of the PEB/OH recycle stream in at least one of said zones in the reactor. Generally, temperatures in the range of from about 370° C. to about 470° C. are employed with benzene to ethylene molar ratios in the range of from about 2:1 to about 20:1; pressures in the range of from about atmospheric to about 25 atmospheres; and benzene WHSV's in the range from about 20 to about 200. An appropriate catalyst such as a zeolite material like silicalite or Mobil ZSM-5 (manufactured by Mobil Oil Corporation New York, N.Y.) is used in the alkylation reactor. These catalysts have been discovered to achieve moderate xylene suppression and acceptable conversion and activity rates.

BRIEF DESCRIPTION OF THE DRAWING

The FIGURE illustrates schematically the alkylation process for manufacturing ethylbenzene from benzene and ethylene.

DESCRIPTION OF THE PREFERRED EMBODIMENTS

The process of the subject invention generally comprises the steps of feeding ethylene and benzene to multiple alkylation reaction zones where the reactants are brought into contact with catalyst materials under alkylation conditions. The catalyst materials are preferably fairly stable and highly selective to the production of ethylbenzene and diethylbenzene in a temperature range of from about 370° C. (700° F.) to about 470° C. (880° F.). A portion of the PEB/OH recycle stream from the distillation column is diverted from the heater and directed into one of the alkylation zones as a quench. Conversion of reactants, as measured by the amount of ethylene actually reacted compared to the amount delivered to the reactor, is high and remains so over commercially acceptable periods of time. Importantly, xylene production can be suppressed dramatically and regeneration of the catalyst delayed significantly.

Referring now to the schematic drawing of the EB conversion process, a 4-bed alkylation reactor (AR), designated at 10, comprises four catalytic reaction beds A, B, C, and D. An ethylene (Eth) feed line 11 provides a fresh supply of ethylene feedstock to reactor 10. Control valves 12-15 allow control of the ethylene feed to various sections of the reactor 10. Benzene, EB, PEB and resid formed in the reactor are withdrawn from the bottom through line 16.

Benzene is supplied to various sections of reactor 10 to react with the ethylene and form the products leaving via line 16. Two sources of benzene are preferably used to supply the reactor. A fresh benzene feedstock is supplied via benzene line 28 which joins a second benzene supply line 27 leading from distillation column C₃, designated at 26. The combined benzene feed moves through line 29 which then divides into a second feed line 30. Benzene passing through line 30 is controlled by valve 33 and divides into three benzene quench lines, 34-36, controlled by flow valves, 37-39. Lines 34-36 provide benzene quench to reactor beds B, C, and D.

Benzene feed passing through valve 32 is heated in heater 18 to about 450° C., passes through control valve 31 and is mixed in line 17 with PEB/OH from column $C_1$, which moves through line 19, through the flue stack of heater 18, and into line 17.

The products of the alkylation reactor (Bz, PEB, EB, and resid) which flow through line 16 are separated in distillation column C₃, with benzene going out the top through line 27, and the remainder going out the bottom via line 24 to distillation column C₂ designated at 23. The final EB product is distilled off in C₂ and delivered via line 25 to the products terminal or styrene monomer facility. PEB and resid flow out the bottom of C₂ via line 22 into distillation column C₁ designated at 20. PEB is distilled off and flowed through the PEB/OH line 19 while resid flows out the bottom of C₁ through line 21.

In a conventional EB process, all of the PEB/OH produced from column C₁ would flow through line 19, the heater flue stack, and line 17 into the top of the alkylation reactor. We have discovered, however, that diverting a portion of the PEB/OH stream as a quench, directed into the middle or lower section of the reactor, and preferably into the "D" bed of the reactor, provides multiple advantageous purposes. This is illustrated in the drawing as Flowline 40, with control valve 41. This diversion of PEB/OH resulted in longer times between catalyst regeneration, increased ethylene conversion, lowered feed/product ratios, and reduction of O, M, and P-xylenes. The improved process resulted in a slightly higher increase in heating costs, but this was negligible compared to the increased efficiency and product gains with the change.

The process can be carried out using a variety of process equipment, including a reactor vessel which defines multiple alkylation zones, each containing appropriate catalyst materials. The benzene and ethylene reactants can be admixed and preheated prior to introduction into the reaction zone where they contact the catalyst beds under reaction conditions further specified hereinbelow. After a controlled residence time in the reaction zone, the converted hydrocarbon charge passes out of the reactor where the ethylbenzene products are collected by cooling and other standard recovery techniques. The excess benzene exiting from the reactor is normally recycled in a conventional manner.

One particular family of catalyst materials, which can be advantageously employed in the process of the subject invention can be characterized as crystalline zeolite materials which are aluminosilicates comprising three dimensional networks of $SiO_4$ and $AlO_4$ tetrahedra joined by the sharing of oxygen atoms. Two types of zeolite type catalysts have been found to be preferable, silicalites and Mobil's ZSM-5.

In general, alkylation zone reaction conditions for the process of the subject invention will include temperatures in the range of from about 300° C. to about 600° C. and preferably in the range of from about 370° C. to 470° C. The zeolite type catalysts are moisture-sensitive and tend to degrade in the presence of moisture (steam), therefore care is taken to prevent the presence of moisture in the reaction.

An excess of benzene to ethylene is normally employed and in general is in the range of from about 2:1 to about 20:1 molar ratio of benzene:ethylene. Since lower benzene:ethylene ratios result in higher percentage of ethylbenzene, lower molar ratios within this range are preferred. Weight hourly space velocities (WHSV's) of benzene employed in the process of the subject invention can be in the range of from about 20 to about 200 with WHSV's in the range of from about 40 to about 150 being preferred. Operating pressures between about atmospheric and 25 atmospheres can be used with a range of from about 10 to about 15 atmospheres being preferred.

The process of the subject invention can be further exemplified through a study of the following example which is not intended to limit the invention in any manner.

EXAMPLE

Benzene and ethylene were introduced into a four-bed reactor utilizing ZSM-5 catalyst, which was substantially identical in makeup to the schematic representation illustrated in the drawing. For the standard run, the benzene to ethylene molar feed ratio was maintained at about 8:1. The benzene WHSV was held at approximately 70, and the pressure maintained in the range of 250–350 PSI. The product streams were analyzed by gas chromatography.

For the test run, PEB/OH was diverted from the overhead of the reactor into the "D" bed at the rate of 60 GPM, compared to none in the standard run. Unit production rates were targeted at 100% for the run and no significant rate changes were made. Data was omitted for days when PEB was rerouted or when unit shutdowns occurred. Twelve days of standard operation and 20 days of PEB to D-bed were averaged to produce the following table:

|  | Standard | Test | Difference (%) |
|---|---|---|---|
| Unit Rate (%) | 101.5 | 101.0 | −0.5 |
| Recycle Rate (gpm) | 186 | 222 | +19.3 |
| PEB to D-Bed (gpm) | 0 | 60 | — |
| Conversion | 99.34 | 99.5 | +0.2 |
| PEBR/EB Ratio | .0097 | .0080 | −17.5 |
| Bz/EB Ratio | .7365 | .7361 | −0.05 |
| Eth/EB Ratio | .2731 | .2714 | −0.62 |
| MP-Xyl A-2105 OH | .132 | .119 | −9.85 |
| O-Xyl A-2105 OH | .012 | .011 | −8.33 |

The EB plant run was started with a 60 GPM diversion of the PEB/OH to the "D" bed and run for nine days. The PEB/OH stream was removed from the "D" bed and returned to the overhead and the plant run for 14 days. The optimum reactor switchover time for regeneration of catalyst is normally 25 days. Instead of switching reactors to regenerate the catalyst, we again switched 60 GPM of the PEB/OH back into the "D" bed and continued running without regenerate for a total of 41 days. The catalyst activity was determined during the trial according to the following formula:

% Conversion =

-continued $$\frac{\text{Moles of EB plus 2} \times \text{moles of DEB}}{\text{Moles of Ethylene Fed to Reactor}} \times 100\%$$

The selectivity was determined according to the following formula:

$$\text{Selectivity} = \frac{\text{Weight EB and DEB}}{\text{Total Product Weight}} \times 100\%$$

An ethylene conversion of 99.5% was maintained during the test runs as compared to an average ethylene conversion of 99.34% during standard runs. Savings from the increased conversion were obvious from a decrease in the losses through ethylene venting from the distillation columns. The residue/product ratios decreased 17.5% in the test run, compared to the standard run, and the Eth/EB ratio was reduced 0.62%, for a significant annual savings in the reactor. A further savings was recognized in the 9.85% reduction in the meta-and para-xylenes and an 8.33% reduction in ortho-xylene. The lowered xylenes in the EB product stream allows more EB for conversion to styrene in the dehydrogenation reactors in the monomer plant.

An increased natural gas consumption was noted for all the EB heaters. Natural gas consumption increased due to the lower vent gas rate and the increased benzene and recycle flows to the heater. As benzene quench is replaced with recycle in the "D"-bed, more benzene is sent through the heater in order to maintain the same total benzene flow. The natural gas consumption increased due to the increased amount of recycle material in the system. The fuel costs were offset by the increased steam production in the associated overhead condensers.

In conclusion, we obtained an increase in conversion, a decrease in feed/product ratios, lower xylene impurities in EB product and increased heater duties. The overall cost of operation with PEB to D-bed is lower than with standard operation. At 100% production rates and 60 gpm PEB to D-bed the reduced operating costs yield an annual savings of $1.25 million.

Thus the invention comprises the improvement in the manufacture of ethylbenzene from ethylene and benzene, wherein a portion of the PEB/OH stream is diverted directly to the "D" bed of the reactor. In the embodiment shown, this comprised approximately one-fourth to one-third of the total PEB/OH stream, (60 GPM diverted from an average total of about 222 GPM). It is believed that one skilled in the art could also obtain beneficial results by utilizing higher or lower percentage diversions of the PEB/OH stream. It should be pointed out that diverting the PEB/OH into the "D" bed increases the total amount of PEB/OH generated in the system, therefore finding an optimum diversion rate requires a balancing of the diverted PEB/OH against the increased total PEB/OH generated in each particular EB plant or facility. We also believe that similar desirable results might be obtainable by diverting part of the PEB/OH into the "C" and/or "B" reactor beds in place of, and also in combination with, the diversion of the "D" bed.

Although a specific preferred embodiment of the present invention has been described in the detailed description above, the description is not intended to limit the invention to the particular forms of embodiments disclosed therein since they are to be recognized as illustrative rather than restrictive and it will be obvious to those skilled in the art that the invention is not so limited. For example, the aforementioned changes in diversion rate and areas of the reactor (beds) to which the diversion of PEB/OH are directed, are changes one skilled in the art would try, given the disclosure herein. Thus, the invention is declared to cover all changes and modifications of the specific example of the invention herein disclosed for purposes of illustration which do not constitute departure from the spirit and scope of the invention.

The embodiments of the invention in which an exclusive property or privilege is claimed are defined as follows:

1. A process for producing ethylbenzene comprising contacting benzene and ethylene under alkylation reaction conditions over a catalyst in a multibed reactor to form reaction products which include polyethylbenzenes and ethylbenzene, distilling the polyethylbenzenes from said reaction products, and recycling said polyethylbenzenes back to said reactor; wherein a first portion of said recycled polyethylbenzene is recycled to the top of said reactor and a second portion is recycled into a different section of said reactor.

2. The process of claim 1 wherein said catalyst is a silicalite catalyst and said multibed reactor has at least three reactor beds.

3. The process of claim 2 wherein said multibed reactor has four reactor beds and said second portion of said polyethylbenzene recycle is fed to the lowermost bed of said reactor.

4. The process of claim 2 wherein said second portion of said recycle polyethylbenzene is recycled into one of the lower beds of said reactor.

5. The process of claim 1 wherein said first portion comprises about three-fourths of the total recycled polyethylbenzenes.

6. The process of claim 1 wherein said second portion comprises about 25 to 30 percent of the total recycled polyethylbenzenes.

7. In a method for manufacturing ethylbenzene from the catalytic reaction of ethylene and benzene in a multibed reactor, wherein polyethylbenzenes which are among the products of said reactor are recovered and recycled to the top of said reactor, the improvement comprising diverting a portion of said recycled polyethylbenzenes from the top of said reactor to a lower section of said reactor.

8. The method of claim 7 wherein said diverted portion comprises about one-fourth to one-third of said total recycled polyethylbenzenes.

9. The method of claim 7 wherein said diverted portion is fed into the lowermost bed of said multibed reactor.

10. The method of claim 7 wherein said diverted portion comprises about 25 to 30 percent of said total recycled polyethylbenzenes.

11. A method for reducing the production of xylene by-products during the catalytic alkylation of benzene to ethylbenzene and polyethylbenzenes in a multibed reactor, said method comprising:
    separating the polyethylbenzenes from the other products coming from said reactor;
    recycling a first portion of said polyethylbenzenes back into the top bed of said reactor; and,
    recycling a second portion of said polyethylbenzenes into a lower bed of said reactor.

* * * * *

UNITED STATES PATENT AND TRADEMARK OFFICE
CERTIFICATE OF CORRECTION

PATENT NO.   : 4,922,053

DATED        : May 1, 1990

INVENTOR(S)  : James N. Waguespack; James R. Butler

It is certified that error appears in the above-identified patent and that said Letters Patent is hereby corrected as shown below:

On the front page of the patent, Appl. No.: 357,381 should read:

--- Appl. No.: 357,384 ---

Signed and Sealed this

Sixteenth Day of April, 1991

Attest:

HARRY F. MANBECK, JR.

*Attesting Officer*    *Commissioner of Patents and Trademarks*